(12) United States Patent
Atwal

(10) Patent No.: US 6,458,835 B2
(45) Date of Patent: *Oct. 1, 2002

(54) METHOD OF INHIBITING OR TREATING CHEMOTHERAPY-INDUCED HAIR LOSS

(75) Inventor: Karnail S. Atwal, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/805,347

(22) Filed: Mar. 13, 2001

Related U.S. Application Data

(63) Continuation-in-part of application No. 09/447,002, filed on Nov. 22, 1999, which is a continuation of application No. 09/119,884, filed on Jul. 21, 1998, now Pat. No. 6,013,668.
(60) Provisional application No. 60/055,568, filed on Aug. 13, 1997, and provisional application No. 60/071,364, filed on Jan. 15, 1998.

(51) Int. Cl.[7] ................ C07C 255/30; A61K 31/275
(52) U.S. Cl. ........................................ 514/524; 558/419
(58) Field of Search ............................ 558/419; 514/524

(56) References Cited

U.S. PATENT DOCUMENTS

| | | |
|---|---|---|
| 4,057,636 A | 11/1977 | Petersen |
| 4,139,619 A | 2/1979 | Chidsey, III |
| 4,596,812 A | 6/1986 | Chidsey, III et al. |
| 5,011,837 A | 4/1991 | Atwal et al. |
| 5,244,664 A | 9/1993 | Godtfredsen |
| 5,578,599 A | 11/1996 | Diani et al. |
| 6,013,668 A | * 1/2000 | Atwal ........................ 514/524 |

FOREIGN PATENT DOCUMENTS

| | | |
|---|---|---|
| EP | 392802 A2 | 10/1990 |
| WO | WO92/09259 | 6/1992 |

OTHER PUBLICATIONS

Meisheri, K.D. et al, "Enzymatic and Non–Enzymatic Sulfation Mechanisms in the Biological Actions of Minoxidil", Biochemical Pharmacology, vol. 45, No. 2 pp. 271–279, 1993.

Buhl, A.E. et al, "Potassium Channel Conductance: A Mechanism Affecting Hair Growth both In Vitgro and In Vivo", J. Invest. Dermatol., vol. 98, No. 3, pp. 315–319, Mar. 1992.

Pettinger, W.A. et al, "Side Efects of Vasodilator Therapy", Suppl. II Hypertension, vol. 11, No. 3, pp. II–34–II–36, Mar. 1998.

* cited by examiner

*Primary Examiner*—Robert W. Ramser
*Assistant Examiner*—Ebenezer Sackey
(74) *Attorney, Agent, or Firm*—Burton Rodney

(57) ABSTRACT

A method for inhibiting hair loss and/or promoting hair growth in chemotherapy and/or radiation therapy patients wherein the (R)-enantiomer of 4-[[(cyanoimino)-[(1,2,2-trimethylpropyl)amino]methyl]amino]benzonitrile is administered prior to, simultaneous with and/or after chemotherapy and/or radiation treatment.

21 Claims, 1 Drawing Sheet

METHOD OF INHIBITING OR TREATING CHEMOTHERAPY-INDUCED HAIR LOSS

REFERENCE TO OTHER APPLICATIONS

Figure 1:
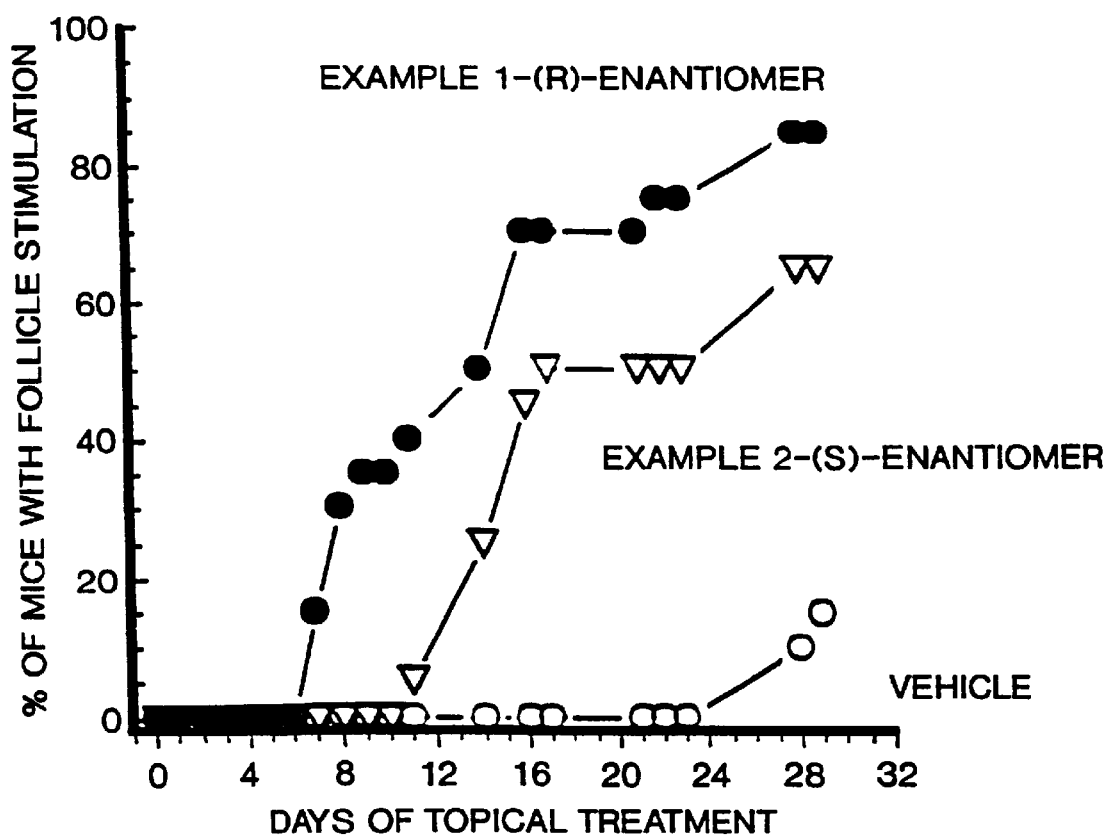

This is a continuation-in-part of U.S. application Ser. No. 09/447,002, filed Nov. 22, 1999, which is a continuation of U.S. application Ser. No. 09/119,884, filed Jul. 21, 1998, now U.S. Pat. No. 6,013,668, which takes priority from Provisional Application No. 60/055,568, Aug. 13, 1997, and Provisional Application No. 60/071,364, Jan. 15, 1998.

FIELD OF THE INVENTION

The present invention relates to a method for inhibiting hair loss and/or promoting hair growth in chemotherapy patients employing the (R)-enantiomer of 4-[[(cyanoimino)[(1,2,2-trimethylpropyl)amino]methyl]amino]benzonitrile or pharmaceutical compositions containing same.

BACKGROUND OF THE INVENTION

Potassium channel openers such as minoxidil (Upjohn), pinacidil (Lilly) and diazoxide (Shiseido and Schering-Plough) are known for their hair growth stimulating activity. Thus, U.S. Pat. Nos. 4,596,812 and 4,139,619 disclose use of minoxidil in the treatment of male pattern baldness, alopecia areata and balding in females. U.S. Pat. No. 4,057,636 discloses pinacidil. DE 3,827,467A discloses combinations of minoxidil and hydrocortisone or retinoids.

U.S. Pat. No. 5,011,837 to Atwal et al discloses aryl cyanoguanidines which possess potassium channel activating activity and are useful therapy for hypertension and other cardiovascular disorders, for various central nervous system disorders, kidney and urinary problems as well as for the promotion of hair growth, for example in the treatment of male pattern baldness (alopecia). These aryl cyanoguanidines have the structure

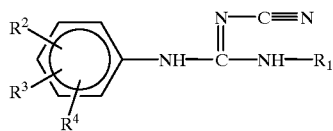

Ia and its possible tautomers

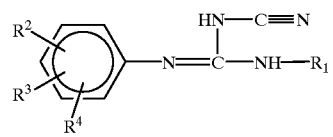

Ib and

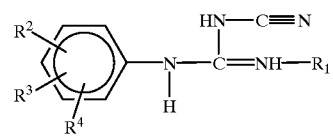

Ic including pharmaceutically acceptable salts, wherein $R_1$ is alkyl, alkenyl, alkynyl, haloalkyl, cycloalkyl, aryl, arylalkyl or cycloalkylalkyl;

$R_2$ is

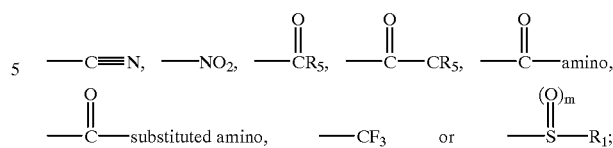

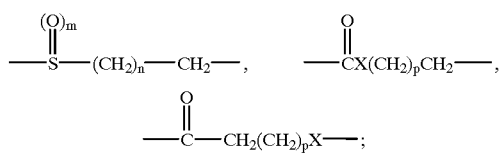

$R_3$ and $R_4$ are each independently selected form $-R_2$, hydrogen, alkyl, alkenyl, alkynyl, haloalkyl, halo, alkoxy, —NHalkyl, —N-(alkyl)$_2$, —S-alkyl, —O-aryl-alkyl, —S-arylalkyl or —S-aryl, —O-aryl, —NHaryl-alkyl, or $R_2$ and $R_3$ taken together are a group which form a ring with the two carbon atoms to which they are attached, which group is selected from

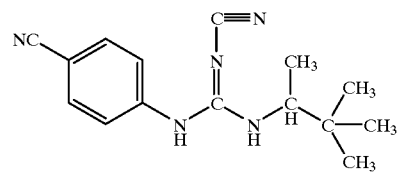

wherein
m=1 or 2,
n=3–5,
p=2–4,
X is O, $NR_5$, $CH_2$; and
$R_5$ is hydrogen or $R_1$.

Example 1 of U.S. Pat. No. 5,011,837 discloses the preparation of 4-[[(cyanoimino)-[(1,2,2-trimethylpropyl)amino]benzonitrile in the form of its racemic mixture.

U.S. Pat. No. 6,013,668 discloses a method for promoting hair growth in humans employing the (R)-enantiomer of 4-[[(cyanoimino)[(1,2,2-trimethylpropyl)-amino]methyl]amino]benzonitrile.

PCT Application WO 92/02225 discloses a combination of a potassium channel opener and a 5-α-reductase inhibitor for promoting hair growth.

PCT Application WO 92/09259A discloses use of an androgen blocker and a potassium channel activator for stimulation of hair growth.

PCT Application WO 96/29988 discloses a topical formulation containing minoxide or minoxidil in combination with a testosterone 5-α reductase inhibitor.

PCT Application WO 94/18936 discloses a method for promoting hair growth employing a vasodilator such as minoxidil in combination with estradiol and/or a 5-α-reductase inhibitor.

The use of minoxidil in cancer patients to decrease the duration of baldness caused by chemotherapy is disclosed by Duvic, M. et al, "A randomized trial of minoxidil in chemotherapy-induced alopecia", J. Am. Acad Dermalol 1996; 35:74–8. Duvic et al disclose that in patients treated with fluorouracil, doxorubicin and cyclophosphamide a 2% topical solution of minoxdil administered during chemotherapy and 4 weeks thereafter, did not prevent alopecia but did decrease period of baldness.

Rodriguez, R. et al "Minoxidil (Mx) as a prophylaxis of doxorubicin-induced alopecia", Annals of Oncology 5:769–770, 1994 discloses that a 2% topical solution of minoxidil was not effective in preventing doxorubicin-induced alopecia.

Hussein, A. M., "Protection Against Cytosine Arabinoside-Induced Alopecia By Minoxidil In A Rat Animal Model", Int. J. Dermatol. Vol. 34(7); 470–3, 1995 discloses that minoxidil, when injected locally, offered good local prevention against 1-B-D-arabinofurano-sylcytosine but not cyclophosphamide-induced alopecia.

DESCRIPTION OF THE INVENTION

In accordance with the present invention, a method is provided for preventing or inhibiting chemotherapy-induced or radiation therapy-induced hair loss wherein a therapeutically effective amount of the (R)-enantiomer of 4-[[(cyanoimino)[(1,2,2-trimethylpropyl)-amino]methyl]amino]benzonitrile, (hereinafter "the (R)-enantiomer") is administered to a human or other mammal.

In addition, in accordance with the present invention, a method is provided for promoting hair growth in a patient undergoing chemotherapy or radiation and/or having chemotherapy-induced hair loss or radiation-induced hair loss, wherein a therapeutically effective amount of the (R)-enantiomer is administered to the patient.

In carrying out the above methods, the (R)-enantiomer will be administered to the patient prior to and/or simultaneously with and/or subsequent to chemotherapy and/or radiation therapy.

The above (R)-enantiomer of the invention has the structure I

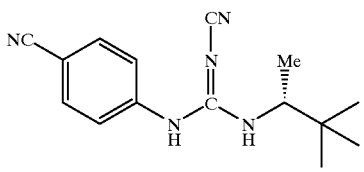

The (R)-enantiomer will preferably be in substantially pure form, that is, will be at least 99% pure (R)-enantiomer and will at most contain 1% (S)-enantiomer.

The method of the present invention also includes the use of pharmaceutical compositions containing the (R)-enantiomer and a pharmaceutically acceptable carrier therefor.

The (R)-enantiomer may be prepared as described in U.S. Pat. No. 6,013,668 which is incorporated herein by reference.

The (R)-enantiomer may be administered by itself or may be administered prior to, simultaneous with or after the antineoplastic agent used in chemotherapy, or prior to simultaneously with or after radiation therapy. In a preferred embodiment of the present invention, the (R)-enantiomer is administered prior to the antineoplastic agent or radiation therapy.

As used herein, the term "simultaneous" means that the antineoplastic agent or radiation therapy and the (R)-enantiomer are administered within 24 hours, preferably 12 hours, more preferably 6 hours, and most preferably 3 hours, of each other.

The chemotherapeutic agent which may be employed with the (R)-enantiomer may include any of the antineoplastic agents listed in the Physician's Desk Reference.

As used herein, the phrase "radiation therapy" includes, but is not limited to, x-rays or gamma rays which are delivered from either an externally applied source such as a beam or by implantation of small radioactive sources.

As used herein, the phrase "antineoplastic agent" refers to compounds which prevent cancer cells from multiplying. In general, the antineoplastic agents of this invention prevent cancer cells from multiplying by: (1) interfering with the cell's ability to replicate DNA, or (2) inducing apoptosis in the cancerous cells.

Examples of antineoplastic agents which are suitable for use in the methods of this invention include, but are not limited to, microtuble-stabilizing agents such as the taxanes, for example, paclitaxel (also known as Taxol®), docetaxel (also known as Taxotere®), 7-O-methylthio-methylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965 filed on Feb. 3, 2000, and example 17 herein), C-4 methyl carbonate paclitaxel (disclosed in WO 94/14787), the epothilone, such as epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]hepta-decane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-di-hydroxy-8,8,10,12,16-pentamethyl-4,17-dioxabi-cyclo[14.1.0]-heptadecane-5,9-dione (disclosed in U.S. Ser. No. 09/506,481 filed on Feb. 17, 2000, and examples 7 and 8 herein), and derivatives thereof; microtuble-disruptor agents; alkylating agents; antimetabolites; epidophyllotoxin; an antineoplastic enzyme; a topoisomerase inhibitor; procarbazine; mitoxantrone; platinum coordination complexes; biological response modifiers; growth inhibitors; hormonal/antihormonal therapeutic agents; and haematopoietic growth factors.

Other classes of antineoplastic agents suitable for use in the method of the present invention include, but are not limited to, the anthracycline family of drugs, the vinca drugs, the mitomycins, the bleomycins, the cytotoxic nucleosides, discodermolide, the pteridine family of drugs, diynenes, aromatase inhibitors, and the podophyllotoxins. Particularly useful members of those classes not previously mentioned include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful antineoplastic agents include estramustine, cisplatin, carboplatin, cyclophosphamide, bleomycin, tamoxifen, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, and interleukins.

In carrying out the method of the invention, the (R)-enantiomer may be formulation with other hair growth promoting compounds such as the potassium channel openers minoxidil (Upjohn) and/or diazoxide (Shiseido and Schering-Plough), as well as cromakalim and pinacidil; a 5-α-reductase inhibitor such as finasteride (Merck's Proscar®), terazosin HCl (Abbott's Hytrin®), or doxaosin mesylate (Pfizer's Cardura®); and/or an androgen blocker such as 4-(5-methoxyheptyl)-hexahydro-2(1H)-pentalenone as disclosed in PCT Application WO 92/09259A, vasoconstrictors such as betamethasone dipropionate, corticosteroids such as hydrocortisone, and scopolamine, and cyproterone acetate.

The (R)-enantiomer may be administered via topical, oral, parenteral or rectal routes as described in U.S. Pat. No. 5,011,837 (incorporated herein by reference), with topical being preferred, to humans or other mammals such as dogs and cats prior to, simultaneously with and/or subsequent to chemotherapy and/or radiation therapy. Thus, the (R)-enantiomer in suitable topical formulations is applied to the skin region where hair growth is desired and/or where hair loss is to be inhibited.

Typical topical formulations for use herein will include conventional ointments, creams, lotions, waxes, gels, pastes, jellies, sprays, aerosols and the like in aqueous or non-aqueous formulations. Examples of suitable topical formulations are disclosed in U.S. Pat. Nos. 4,139,619 and 4,596,812 which are incorporated herein by reference.

The (R)-enantiomer will be used in an effective amount, that is, in an amount sufficient to inhibit hair loss during chemotherapy and/or radiation therapy and/or promote hair growth during and/or subsequent to chemotherapy and/or radiation therapy, such that hair growth is increased or produced. A typical topical composition will include from about 0.01 to about 15% by weight, preferably from about 0.1 to about 10% by weight of the composition.

The topical formulations containing the (R)-enantiomer of the invention can be applied to the area to be treated such as the scalp in humans, by spraying, dabbing or swabbing to deliver the enantiomer to the region of the hair follicle. The formulations will be applied to the area of treatment on a routine basis prior to, during and subsequent to chemotherapy and/or radiation therapy, at least once daily, and preferably two or more times daily.

The accompanying Figure is a graph showing the effect of a once daily application of each of the (R)- and (S)-enantiomers described herein on hair growth in male C3H mice.

The following Example describes the preparation of the (R)-enantiomer and the (S)-enantiomer.

EXAMPLE 1

(R)-4-[[(Cyanoimino)[(1,2,2-trimethylpropyl)amino]-methyl]amino]benzonitrile

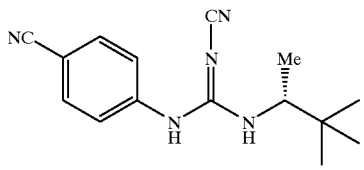

A. (R)-1,2,2-Trimethylpropyl amine

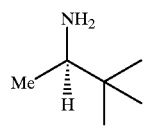

The title compound was prepared according to the procedure described by Manley and Quast (*J. Med. Chem.* 1992, 35, 2327–2340) with some modification. A mixture of pinacolone (29 g, 290 mmol), (R)-α-methylbenzyl amine (17.6 g, 145 mmol) and p-toluenesulfonic acid monohydrate (300 mg) in toluene (150 mL) was refluxed using a Dean-Stark trap (to remove water from the reaction mixture) for 3 days. The solvent was evaporated and the residue was distilled at ca. 120-2° C. (9 mm) to give 21 g (71% yield) of

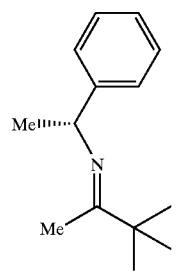

as a colorless oil. This material was dissolved in anhydrous THF (210 mL) and treated at 0–2° C. with borane-THF complex (1M, 206 mL, 206 mmol). The mixture was allowed to come to room temperature, stirred for 5 h and concentrated in vacuo. To the resulting oily residue was carefully added ethanol (300 mL), and the mixture was refluxed for 1 h and concentrated again in vacuo. The residue was chromatographed over basic alumina (activity grade 1/hexane) giving colorless oil. Proton NMR and HPLC (YMC Cl8 S3 4.6X50 mm column/water-MeOH—H$_3$PO$_4$ 90:10:0.2 to 10:90:0.2 gradient) indicated that this material was contaminated with ca. 10% of the (S,R)-diastereomer. Therefore, this mixture was resubjected to flash chromatography (silica gel/hexane-EtoAc-triethylamine 95:5:0.1) to afford

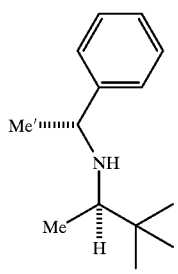

(11.45 g, 55.8 mmol, 54% yield). The above compound (11.45 g) and 10% palladium on carbon (1.5 g) were taken in EtOH (230 mL) and stirred under hydrogen for 12 hours. The mixture was filtered and the filtrate (ca. 230 mL) containing the title product was used as such for the next step as a ca. 0.24 M solution in ethanol (assumed 100% yield).

B. N-Cyano-N'-(4-cyanophenyl)thiourea, monosodium salt

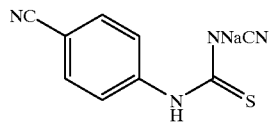

The title compound was prepared according to Example 1 Part A of U.S. Pat. No. 5,011,837.

C. (R)-4-[[(Cyanoimino)[(1,2,2-trimethyl-propyl)amino]methyl]amino]benzonitrile

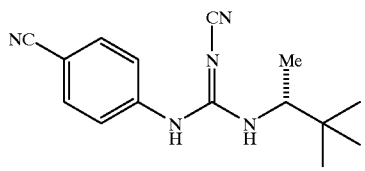

To a solution of Part B compound (6.0 g, 26.8 mmol) in DMF (150 mL) was sequentially added the solution of Part A compound (ca. 0.24 M in EtOH, 112 mL, 26.8 mmol) and 1-(3-dimethylamino-propyl)-3-ethylcarbodiimide hydrochloride (WSC) (6.0 g, 31.3 mmol). The mixture was stirred at room temperature for 3 hours, diluted with ethyl acetate and sequentially washed with 1N HCl, water and brine. The organic layer was dried over magnesium sulfate, concentrated and the crude product was purified by flash chromatography on silica gel (hexanes-ethyl acetate-triethylamine 75:25:0.2) to afford a colorless foam. This material was recrystallized from isopropanol to give the title compound as a white solid (4.15 g, 57.6%), mp 159–60° C.; $[\alpha]_D$ –180° C.=1, MeOH; enantiomeric purity determined by chiral HPLC=99% (ChiralPak AD column/hexane-isopropanol-triethylamine 80:20:0.2); MS: 270 (M+H)$^+$; $^1$H NMR (CDCl$_3$) δ 8.65 (br s, 1H), 7.69 (d, 2H, J=8.79 Hz), 7.37 (d, 2H, J=8.79 Hz), 4.93 (br d, 1H), 3.83 (m, 1H), 1.10 (d, 1H, J=6.45 Hz), 0.90 (s, 9H).

Elemental analysis: calculated for $C_{15}H_{19}N_5$:
C, 66.89; H, 7.11; N, 26.00
Found: C, 66.71; H, 7.14; N, 25.98.

EXAMPLE 2
(S)-4-[[(Cyanoimino)[(1,2,2-trimethylpropyl)amino]methyl]amino]benzonitrile

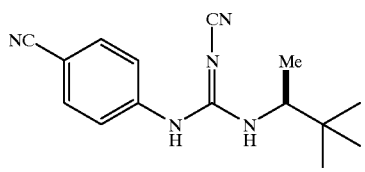

The title compound was prepared from Part B compound of Example 1 and (S)-1,2,2-trimethylpropyl amine (prepared according to Manley and Quast, *J. Med. Chem.*, 1992, 35, 2327–2340) by the same procedure as described in Example 1, Part C. The product was obtained as a colorless solid, mp 158–59° C.; $[\alpha]_D$ +189° C.=1, MeOH; enantiomeric purity determined by chiral HPLC=99.4% (ChiralPak AD column/hexane-isopropanol-triethylamine 80:20:0.2); MS: 270 (M+H)$^+$; $^1$H NMR (CDCl$_3$) δ 8.43 (br s, 1H), 7.69 (d, 2H, J=8.79 Hz), 7.37 (d, 2H, J=8.79 Hz), 4.93 (br d, 1H), 3.83 (m, 1H), 1.10 (d, 1H, J=6.45 Hz), 0.90 (s, 9H).

EXAMPLE 3
Comparison of Example 1-(R)-Enantiomer and Example 2-(S)-Enantiomer Re Hair Growth in an Animal Model The objective of the following described experiment was to compare and evaluate the in vivo effect of the Example 1-(R)-enantiomer and the Example 2-(S)-enantiomer on hair growth in an animal model. The two enantiomers were compared topically for hair growth in C3H mice.

Animal Model

The C3H mouse is a useful model for studying hair growth. Its usefulness rests with the fact that skin pigmentation of this animal is provided by the melanocytes of the hair follicle and not the epidermis. In the telogen or the resting phase of the hair follicle, the skin is pink. In the earliest phase of anagen or the growth phase, there is sudden graying of the skin and as the anagen phase progresses the skin becomes darker in color. In this study, visual observation was used as an in vivo assay of anagen induction. Furthermore as anagen develops, the skin thickness increases from a thin telogen skin to a measurably thickened anagen skin. Thus, recording the skin color and microscopic thickness of skin from these mice offers a sensitive, quantifiable and convenient method of assessing the phases of hair growth.

Groups of 20, six to seven week old male C3H mice with hair follicles in the resting phase of hair growth were used. At this stage in their life, the hair follicles remain in the telogen phase for up to 30 days or longer. This provides an adequate window of time to screen drugs. Compounds that improve hair growth stimulate the hair follicles from the telogen to the anagen phase. This stimulation is manifested by the shortening of the telogen phase of the hair follicle cycle.

Animals were anesthetized with ketamine/rompun (100 mg/Kg and 12 mg/Kg) IP and the hair over a defined dorsal area were closely clipped.

Animals with pink skin were treated topically 1x daily, 5 days per week with 50 microliters of a 2% solution of Example 1-(R)-enantiomer and a 2% solution of Example 1-(S)-enantiomer or vehicle by itself, applied to the dorsal area. The vehicle employed was ethanol/propylene glycol/water, 60/30/10. Treatment was continued for at least 4–5 weeks.

Animals were observed daily for side effects and changes to the test sites. All observations were documented. Test sites were graded weekly for changes in skin color and hair growth. In this study drug effects were evaluated using the visual observation of skin changing from pink to gray and resulting in hair growth.

Results

The percent of animals that induced hair follicle stimulation during the treatment period is illustrated in the accompanying Figure below. The most significant observation made between the two enantiomers is the difference in the time of onset of follicle stimulation. The time of onset for the Example 1-(R)-enantiomer was day 7 compared to day 11 for Example 2-(S)-enantiomer. The time of onset for the vehicle control was day 28. By day 11 of treatment the Example 1-(R)-enantiomer caused hair follicle stimulation in 40% of the test mice compared to only 5% with Example 2-(S)-enantiomer. By day 14, 50% of the animals treated with Example 1-(R)-enantiomer showed hair follicle stimulation compared to 25% for Example 2-(S)-enantiomer. By day 28, 85% of the animals treated with the Example 1-(R)-enantiomer showed hair follicle stimulation as compared to 65% treated with Example 2-(S)-enantiomer. Thus throughout the treatment period, the group treated with Example 1-(R)-enantiomer showed a higher incidence of hair follicle stimulation as compared to the group treated with Example 2-(S)-enantiomer.

The attached Figure shows the effect of 1× daily topical application of Example 1-(R)-enantiomer and Example 2-(S)-enantiomer.

In conclusion, these results in the C3H mice indicate that there is a remarkable difference between the Example 1-(R)-enantiomer and the Example 2-(S)enantiomer in their effect on hair follicle stimulation; in particular the (R)-enantiomer has a faster onset of action compared to the corresponding (S)-enantiomer.

These results are indeed surprising and unexpected especially in view of the vasorelaxant potencies of each of these enantiomers, which is generally recognized as an indication of hair growth promoting properties (Side Effects of Vasodilator Therapy, W. A. Pettinger et al, Hypertension, 1988, Vol. 11, II-34 to II-36, and Minoxidil Stimulates Cutaneous Blood Flow in Human Balding Scalps: Pharmacodynamics measured by laser Doppler velocimetry and photopulse plethysmography. R. C. Wester et al, J. Invest. Dermatol., 184, Vol. 82, 515–517).

Thus, while the $IC_{50}$ for vasorelaxant potency of the (R)-enantiomer is 47±17 nM versus 157±35 nM for the (S)-enantiomer, as seen above, the hair growth promoting ability of the (R)-enantiomer for producing hair growth within 11 days of treatment is 8 times greater than the corresponding (S)-enantiomer.

What is claimed is:

1. A method for promoting hair growth in a patient having chemotherapy-induced hair loss or radiation-induced hair loss, which comprises administering to a human or other mammal a therapeutically effective amount of the (R)-enantiomer of 4-[[(cyanoimino)[(1,2,2-trimethylpropyl)amino]methyl]amino]benzonitrile.

2. The method as defined in claim 1 wherein the (R)-enantiomer is administered prior to, or subsequent to chemotherapy or radiation therapy.

3. The method as defined in claim 1 wherein the (R)-enantiomer is administered prior to chemotherapy or radiation therapy.

4. The method as defined in claim 1 wherein the (R)-enantiomer is administered subsequent to chemotherapy or radiation therapy.

5. The method as defined in claim 1 wherein the (R)-enantiomer is administered topically.

6. The method as defined in claim 1 wherein the (R)-enantiomer is administered as a cream formulation, lotion formulation, liquid formulation or ointment formulation.

7. The method as defined in claim 1 wherein the (R)-enantiomer is administered systemically.

8. The method as defined in claim 1 for promoting hair growth in a patient having chemotherapy-induced hair loss.

9. The method as defined in claim 1 for promoting hair growth in a patient having radiation-induced hair loss.

10. The method according to claim 1 wherein the (R)-enantiomer is administered in conjunction with a chemotherapeutic agent.

11. The method according to claim 1 wherein the (R)-enantiomer is administered in conjunction with a chemotherapeutic agent which is an antineoplastic agent selected from the group consisting of an anthracycline drug, a vinca drug, a mitomycin, a bleomycin, a cytotoxic nucleoside, a taxane, an epothilone, discodermolide, a pteridine drug, a diynene, an aromatase inhibitor and a podophyllotoxin.

12. The method according to claim 1 wherein the (R)-enantiomer is administered in conjunction with a chemotherapeutic agent which is an antineoplastic agent selected from the group consisting of paclitaxel, docetaxel, 7-O-methylthiomethyl-paclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*, 16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecase-5,9-dione, [1S-[1R*,3R*(E),7R*,10S*,11R*, 12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, vindesine, leurosine, estramustine, cisplatin, carboplatin, cyclophosphamide, bleomycin, tamoxifen, ifosamide, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, a pyridobenzoindole, an interferon and an interleukin.

13. The method as defined in claim 1 wherein the (R)-enantiomer is administered in the form of a topical formulation comprising ethanol, propylene glycol and water.

14. The method as defined in claim 13 wherein the ethanol/propylene glycol/water are in a 60/30/10 proportion.

15. The method as defined in claim 1 wherein the (R)-enantiomer is administered in an amount from about 0.01 to about 15% by weight of said (R)-enantiomer.

16. The method as defined in claim 1 wherein the (R)-enantiomer is administered in the form of ethanol/propylene glycol/water, 60/30/10, is an amount to provide a 2% solution of the (R)-enantiomer.

17. The method as defined in claim 1 wherein the (R)-enantiomer is administered in combination with one or more other hair growth promoting agents.

18. The method as defined in claim 17 wherein said other hair growth promoting agent is another potassium channel opener, a 5-α-reductase inhibitor, an androgen blocker, betamethasone dipropionate, a corticosteroid, scopolamine and/or cyproterone acetate.

19. The method as defined in claim 18 wherein the other potassium channel opener is minoxidil, diazoxide, cromakalim and/or pinacidil; the 5-α-reductase inhibitor is finasteride, terazosin HCl, and/or doxaosin mesylate; the androgen blocker is 4-(5-methoxyheptyl)-hexahydro-2(1H)-pentalenone; and the corticosteroid is hydrocortisone.

20. The method as defined in claim 19 wherein said other hair growth promoting agent is a 5-α-reductase inhibitor.

21. The method as defined in claim 20 wherein the 5-α-reductase inhibitor is finasteride.

* * * * *